US009017278B2

(12) United States Patent
Nakamura

(10) Patent No.: US 9,017,278 B2
(45) **Date of Patent: *Apr. 28, 2015**

(54) COVER FOR GAS MIST PRESSURE BATH

(75) Inventor: Shoichi Nakamura, Higashichikuma-gun (JP)

(73) Assignees: ACP Japan Co., Ltd., Tokyo (JP); Shoichi Nakamura, Higashichikuma-gun, Nagano (JP)

( * ) Notice: Subject to any disclaimer, the term of this patent is extended or adjusted under 35 U.S.C. 154(b) by 492 days.

This patent is subject to a terminal disclaimer.

(21) Appl. No.: 12/736,422

(22) PCT Filed: Dec. 25, 2009

(86) PCT No.: PCT/JP2009/071532

§ 371 (c)(1), (2), (4) Date: Oct. 7, 2010

(87) PCT Pub. No.: WO2010/074196

PCT Pub. Date: Jul. 1, 2010

(65) Prior Publication Data

US 2011/0046545 A1 Feb. 24, 2011

(30) Foreign Application Priority Data

| | | |
|---|---|---|
| Dec. 26, 2008 | (JP) | 2008-009179 U |
| Dec. 26, 2008 | (JP) | 2008-009180 U |
| Mar. 10, 2009 | (JP) | 2009-001396 U |
| Mar. 10, 2009 | (JP) | 2009-001397 U |

(51) Int. Cl.
*A61M 37/00* (2006.01)
*A61H 35/00* (2006.01)
(Continued)

(52) U.S. Cl.
CPC ................ *A61H 35/00* (2013.01); *A61H 33/10* (2013.01); *A61H 33/14* (2013.01);
(Continued)

(58) Field of Classification Search
CPC ....... A61H 33/14; A61H 33/10; A61H 35/00; A61H 2001/165; A61H 2033/143; A61H 2033/145; A61H 2205/10; A61H 2205/12; A61H 2205/161
USPC ........................................................ 604/23–24
See application file for complete search history.

(56) References Cited

U.S. PATENT DOCUMENTS

| | | | | |
|---|---|---|---|---|
| 5,000,164 | A * | 3/1991 | Cooper | 601/11 |
| 5,154,697 | A * | 10/1992 | Loori | 604/23 |
| 5,810,795 | A * | 9/1998 | Westwood | 604/305 |
| 6,638,270 | B2 * | 10/2003 | Johnson | 604/890.1 |

(Continued)

FOREIGN PATENT DOCUMENTS

| | | |
|---|---|---|
| JP | S61-217132 | 9/1986 |
| JP | 2005-058745 | 3/2005 |
| JP | 3144717 U | 9/2008 |
| WO | WO2008/047829 | 4/2008 |

*Primary Examiner* — Edelmira Bosques
(74) *Attorney, Agent, or Firm* — Manabu Kanesaka

(57) ABSTRACT

A cover for a gas mist pressure bath includes a bag shaped living-body cover member for covering the skin and mucous membrane of the living body; a tightening device disposed at one side of the living-body cover member to tighten an opening of the living-body cover member to prevent diffusion of the gas mist; a gas mist supply port communicating with an inside of the cover for the gas mist pressure bath for introducing the gas mist into the cover; an outlet attached to the living-body cover member for exhausting air, the gas mist or gas sealed in the cover for the gas mist pressure bath and controlling quantity of the air, gas mist, or gas, and a pressurizing device disposed on another side of the living-body cover member for pressurizing the inside of the living-body cover member, wherein when the pressurizing device is operating, a pressurization is applied.

1 Claim, 12 Drawing Sheets

(51) Int. Cl.
*A61H 33/10* (2006.01)
*A61H 33/14* (2006.01)

(52) U.S. Cl.
CPC .... *A61H 2033/143* (2013.01); *A61H 2033/145* (2013.01); *A61H 2201/165* (2013.01); *A61H 2205/065* (2013.01); *A61H 2205/10* (2013.01); *A61H 2205/12* (2013.01)

(56) References Cited

U.S. PATENT DOCUMENTS

| | | | | |
|---|---|---|---|---|
| 6,652,479 | B2 * | 11/2003 | Rasor et al. | 604/23 |
| 2005/0043672 | A1 * | 2/2005 | Piuk et al. | 604/23 |
| 2005/0137521 | A1 * | 6/2005 | Stenzler | 604/23 |
| 2011/0028888 | A1 * | 2/2011 | Nakamura | 604/24 |

* cited by examiner

COVER FOR GAS MIST PRESSURE BATH

RELATED APPLICATIONS

The present application is National Phase of International Application No. PCT/JP2009/074196 filed Dec. 25, 2009, and claims priorities from, Japanese Applications No. U-2008-009179 filed Dec. 26, 2008; No. U-2008-009180 filed Dec. 26, 2008; No. U-2009-001396 filed Mar. 10, 2009; and No. U-2009-001397 filed Mar. 10, 2009, the disclosure of which are hereby incorporated by reference herein in its entirety.

TECHNICAL FIELD

The present invention relates to a cover for a gas mist pressure bath used for taking a gas mist pressure bath, in which a mist (called as "gas mist" hereafter) is prepared by pulverizing and dissolving carbon dioxide or oxygen or a mixed gas (called as "gas" hereafter) of carbon dioxide and oxygen, and liquid, and the thus prepared gas mist is directly contacted to a skin and mucous membrane of a human living-body at pressure of not less than a predetermined value.

BACKGROUND ART

It has conventionally been known that carbon dioxide (carbonic acid anhydride: $CO_2$, called as "carbon dioxide" hereafter) has both properties of being not only soluble in water (water-soluble) but also soluble in fat (fat-soluble) and, therefore, by only contacting the skin and mucous membrane of the living-body being like mixed with water and fat, carbon dioxide penetrates under a subcutaneous layer and expands blood vessels around parts of penetrated carbon dioxide, and it works to improve a blood circulation. Owing to this action of accelerating the blood circulation, it displays various physiological effects such as dropping of blood pressure, improving of metabolism or accelerating to remove pain substance or waste product. Further, it has also anti-inflammation and anti-bacterial. Therefore, carbon dioxide has recently been given attentions also from viewpoints of improving health or beauty other than the purpose of medical cares.

Carbon dioxide in the tissue of the living-body works to release oxygen carried in combination with hemoglobin in a red blood cell. Around parts at a high density of carbon dioxide, the red blood cell releases more oxygen. Thus, supply of oxygen to cells by the red blood cell is mainly controlled by carbon dioxide. In short, being without carbon dioxide, hemoglobin remains as combined with oxygen and the cell becomes unable to receive oxygen. As is seen, carbon dioxide seems to be a waste product resulted from action of oxygen, however, it plays in fact very important roles in the human living-body.

Further, in recent times, oxygen of high density has also widely been known as effective in activity of metabolism, accelerating the blood circulation, fatigue recovery, or stability of blood pressure. Other than them, oxygen has disinfection or sterilization by oxidative effect.

Therefore, for causing to directly absorb carbon dioxide or oxygen into a living body, an inventor of this invention has proposed a gas mist pressure bath device and a gas mist pressure bath system using the cover for the gas mist pressure bath.

SUMMARY OF INVENTION

Problems to be Solved by the Invention

However, the conventional bag shaped cover for the gas mist pressure bath was involved with problems of requesting time for taking off a tightening part or stopper of the cover each time when exhausting air, gas or a gas mist within the cover. Further, also, when pressure within the cover for the gas mist pressure bath became too high, similarly, the tightening part or stopper were once taken off, and the gas mist had to be again fed.

In view of the above circumstances, it is an object of the present invention to provide a cover for the gas mist pressure bath which causes gas of even a small amount to be efficiently absorbed into the skin and mucous membrane of the living body, and which can also easily exhaust air, gas or the gas mist within the cover for the gas mist pressure bath, or adjust pressure within the cover.

Means for Solving the Problem

For solving the above mentioned problems, the present invention is to provide the cover for the gas mist pressure bath (often called, hereafter, as "the gas mist pressure bath cover", "the cover member", or merely "the cover" as the case may be), in which a mist (called as "gas mist" hereafter) is prepared at a density of not less than a predetermined value by pulverizing and dissolving carbon dioxide or oxygen or a mixed gas (called as "gas" hereafter) of carbon dioxide and oxygen and liquid, and the thus prepared gas mist is sealed in the cover and is directly contacted to the skin and mucous membrane of the living-body, and the cover for the gas mist pressure bath comprises a bag shaped living-body cover member for covering the skin and mucous membrane of the living body; a tightening means furnished at an opening of the living-body cover member and tightening the opening to prevent diffusion of the gas mist; a gas mist supply port communicating with the inside of the cover for the gas mist pressure bath for introducing the gas mist into the cover for the gas mist pressure bath; and an outlet for exhausting air, the gas mist or gas sealed in the cover for the gas mist pressure bath to adjust the amounts thereof.

By the way, the invention refers it as "pulverizing and dissolving" to pulverize liquid into fine liquid drops, and cause to contact and mix with gas (carbon dioxide, or oxygen, or mixed gas of carbon dioxide and oxygen).

Herein, the cover for the gas mist pressure bath according to the present invention is desirably further provided with a pressurizing means for pressurizing the inside of the living-body cover member.

The gas mist supply port has a check valve inside thereof.

Further, the tightening means is desirably made of any one of or plural combination of rubber, string or face fastener.

Preferably, there is/are provided one or plural adhesive means having viscosity to the living-body's skin and mucous membrane on the face of the living-body cover member contacting the skin and mucous membrane.

The living-body cover member has desirably a glove-shape for covering, at least, the fingers, palm, back of the living-body' hand, and a shape of a gauntlet for covering a forearm, otherwise, a sock-shape for covering the fingers, sole and instep of a living-body's foot, and further, for covering heel, or lower extremity.

The pressurizing means is composed of an air storage communicating with the cover member, and pressurizes the gas mist and gas in the air storage and exhausts them into the cover member to carry out pressurization. Between the air storage and the living-body cover member, there is desirably provided a connection part having a check valve inside thereof.

Otherwise, the pressurizing means is composed of a reducing means of the living-body cover member, so that the reducing means may reduce the cover member at its end to carry out pressurization.

The pressurizing means is composed of a ring member, and owing to its shrinkage, the over member may be pushed on its outer circumference by means of the inner circumference of the ring member.

The pressurizing means is composed of a shielding film made of an elastic member sectioning the inside of the cover member into an insertion side of the living-body and an air storage, the air storage sectioned by the shielding film, and a pump connected to the air storage, and by sending gas from the pump into the air storage, the shielding film is expanded from the air storage to the insertion side of the living-body to carry out pressurization.

Advantageous Effect of the Invention

Depending upon the present invention, not requiring a much amount of gas, while exhausting air within the cover for the gas mist pressure bath, and easily adjusting pressure in the cover, it is possible to cause the gas mist to be absorbed into the skin and mucous membrane of the living body.

DESCRIPTION OF EMBODIMENTS

In the following description, explanations will be made to embodiments of this invention in detail, referring to the attached drawings.

First Embodiment

Figure 1:
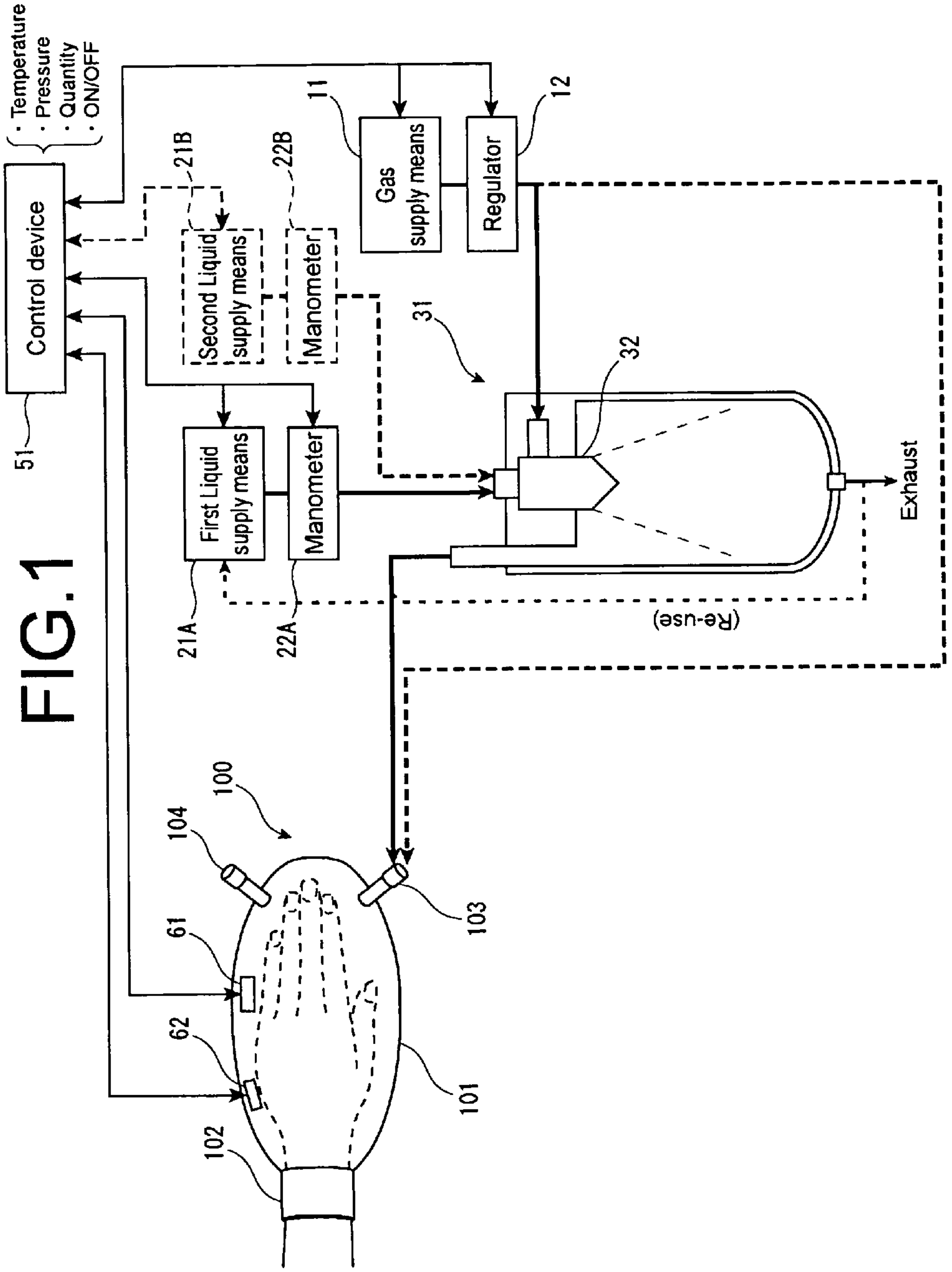
FIG. 1 A typical view showing one example of the gas mist pressure bath system applied with the cover for the gas mist pressure bath depending on a first embodiment of the invention.

The gas mist pressure bath system of this embodiment applying the cover for the gas mist pressure bath will be referred to. FIG. 1 is the typical view showing one example of the gas mist pressure bath system. As shown in this view, the gas mist pressure bath system of this embodiment comprises a gas supply means 11, a liquid supply means 21, a gas mist supply device 31 for generating and supplying the gas mist prepared by pulverizing and dissolving liquid and gas (carbon dioxide or oxygen or the mixed gas of carbon dioxide and oxygen), the cover 100 for the gas mist pressure bath forming a space of sealing inside the supplied gas mist, and a control device 51 for generating and controlling to supply the gas mist.

The gas mist supply means 11 supplies gas to the gas mist supply means 31, provided that if the mist is enough supplied in the cover 100 for the gas mist pressure bath, only gas is directly supplied into the cover 100 from the gas mist supply means 11. It is optimum to use a gas bomb as the gas mist supply means 11. The gas mist supply means is provided with a regulator 12 for controlling gas pressure. Omitting to show, the gas supply means 11 may be disposed with a heater for heating gas or a thermometer for controlling temperatures.

The liquid supply means 21 is composed of a pump or the like and supplies liquid to the gas mist supply device 31. As the liquid, it is suitable to use water, ionic water, physiological salt solution, ozone water, purified water or sterilized water. Further, these liquids may contain medicines useful to user's diseases or symptoms. For the medicines, enumerated are, for example, anti-allergic agent, anti-inflammatory agent, anti-febrile, anti-fungus agent, anti-influenza virus, carcinostatic substance, anti-hyper tensive agent, cosmetic agent, or trichogen. Further, these liquids are further possible to generate synergistic effects by coupling with a gas physiological action with single or plurality of menthol having a cooling action; vitamin E accelerating circulation of the blood; vitamin C derivative easily to be absorbed to a skin tissue and having a skin beautifying effect; retinol normalizing a skin heratinizing action and protecting the mucous membrane; anesthetic moderating irritation to the mucous membrane; cyclodextrin removing odor; photocatalysis or a complex of photocatalysis and apatite having disinfection and anti-phlogistic; hyaluronic acid having excellent water holding capacity and a skin moisture retention effect; coenzyme Q10 activating cells and heightening immunization; a seed oil containing anti-oxidation and much nutrient; or propolith having anti-oxidation, anti-fungus, anti-inflummatory agent, pain-killing, anesthetic, and immunity. Otherwise, the liquids may be added with ethanol, gluconic acid chlorohexizine, amphoteric surface active agent, benzalkonium chloride, alkyldiamino ether glycin acetate, sodium hypochlorite, acetyl hydroperoxide, sodium sesquicarbonate, silica, povidone-iodine, sodium hydrogen carbonate. In addition, high density carbonate spring may be added (as examples organic components, sulfate, carbonate, sodium dichloroisocyanurate).

Further, as shown in FIG. 1, plural liquid supply means 21A, 21B are arranged for respectively different liquids. The liquid supply means 21 is furnished with pressure gauges 22 (22A, 22B) respectively for controlling supplying pressure.

In addition, it is desirable to dispose a heater (not shown) heating the liquid (for example, heating to a hot water of around 40° C.) or a thermometer (not shown).

The gas mist supply device 31 is for supplying under pressure the gas mist into the living-body pressure bath cover 100, the gas mist being prepared by pulverizing and dissolving the liquid from the liquid supply means 21 and gas from the gas supply means 11. Gas is accelerated in absorption into the skin and mucous membrane by supplying under a condition of the gas mist of pulverizing and dissolving together with liquid. Size of the mist is desirably less than 10 μm. Herein, there is shown an example of the gas mist generated by using high speed flow of gas supplied from the gas supply means 11 by the fluid nozzle 32. Other than this, there may be used gas mist supply devices of various systems such as jetting gas at high pressure into liquid to generate the gas mist, or utilizing super sonic wave to generate the same.

The control device 51 is composed of a computer having CPU, memory and display. This performs under an optimum condition various kinds of controls such as pressure control or on-off switch of gas supplied from the gas supply means 11; gas supply to the gas mist supply means 31/the cover 100 for the gas mist pressure bath; supply pressure control and temperature control of liquid from the liquid supply means 21; and on-off switch of supply from the gas mist supply means 31. In particular, it is preferable to compose a structure as stopping of supplying of gas of the gas supply means 11 by the control device 51, when the pressure value within the cover 100 becomes more than a predetermined value.

Figure 2:
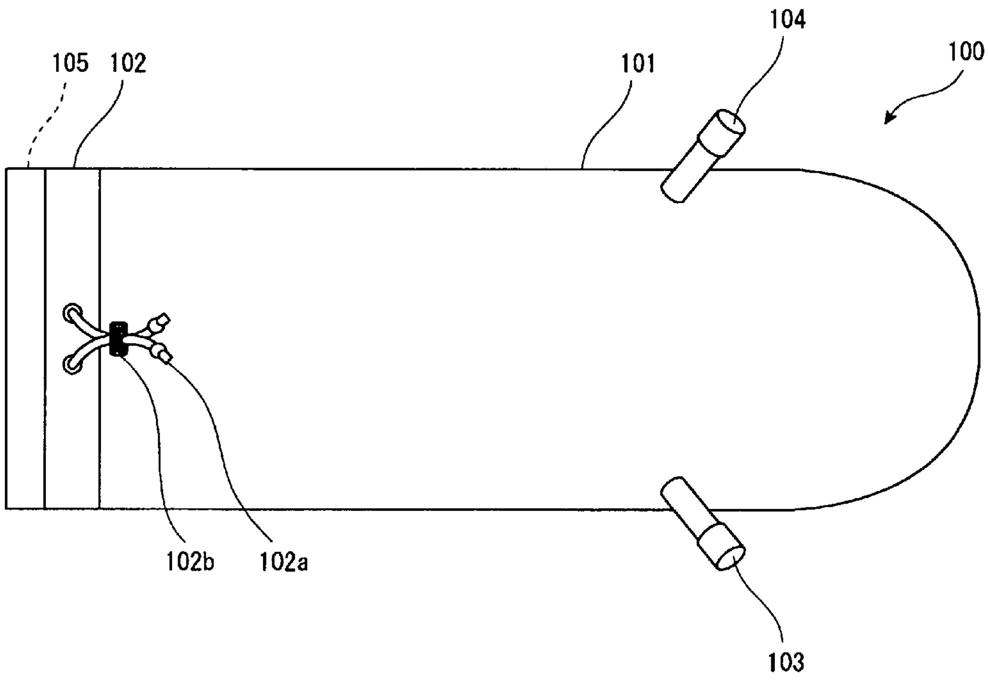
FIG. 2 A generally schematic view of the cover for the gas mist pressure bath depending on the first embodiment of the invention.
Figure 3:
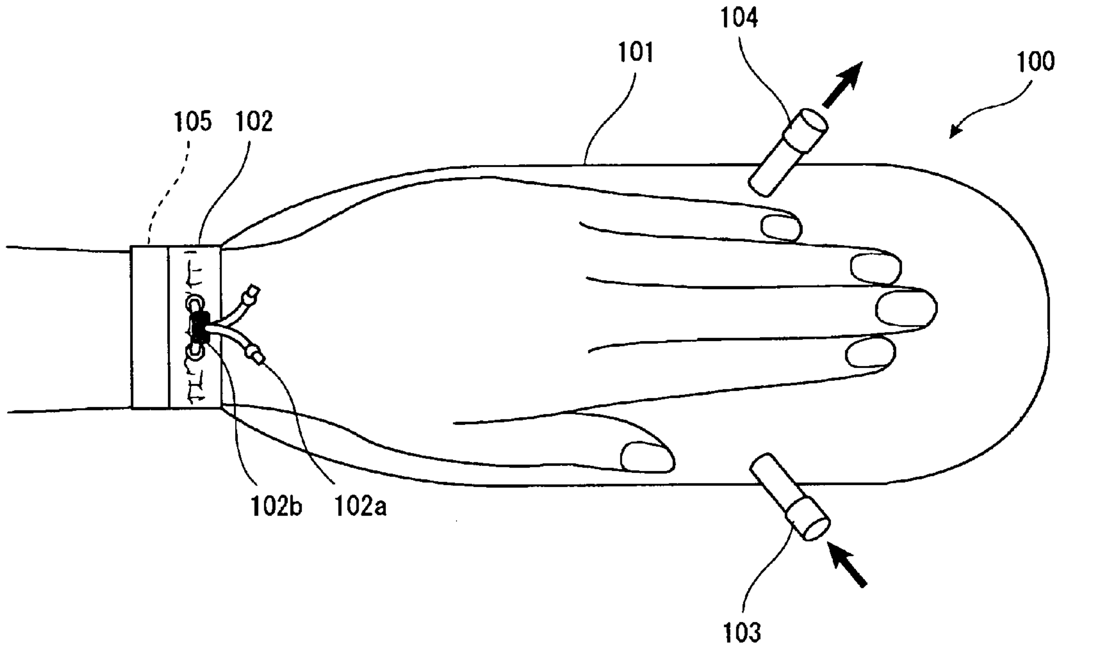
FIG. 3 A typical view showing an attaching condition of the cover for the gas mist pressure bath depending on the first embodiment of the invention.

The cover 100 for the gas mist pressure bath can cover the skin and mucous membrane of the living body (herein, as the examples, the living body's hand) and form a space for sealing the gas mist and gas inside thereof. FIG. 2 is the generally schematic view of the cover for the gas mist pressure bath depending on the first embodiment of the invention, and FIG. 3 is the typical view showing the attaching condition of the cover for the gas mist pressure bath.

The cover 100 is, as shown in them, composed of the bag shaped living-body cover member 101 for covering the skin and mucous membrane of the living body, a tightening means 102 furnished at the opening of the cover member 101, closing to prevent diffusion of the gas mist and gas, a gas mist supply port 103 for leading the gas mist and gas inside of the living-body cover member 101, and an outlet 104 for controlling the amounts of air, the gas mist or gas in the cover member 101 or exhausting them.

The living-body pressure bath cover 101 is composed of the bag member having a size enabling to cover parts of the living body (herein, as the example, the living body's hand). The living-body cover member 101 is made of the woven or non-woven fabric of a pressure resistant, non-air permeable and non-moisture permeable materials, for example, preferably, the natural rubber, silicone rubber, polyethylene, polypropylene, polyvinylidene, polystylene, polyvinylacetate, polyvinyl chloride, polyamide resin, polytetrafluoroethylene.

The living-body cover member 101 is furnished at its opening with the tightening means 102 to prevent the gas mist and gas from diffusing. Herein, as the example, the tightening means 102 is composed of a string 102*a* and a string stopper 102*b*. Other than the string 102*a*, a rubber or a face fastener may compose the tightening means by a single or plural combination.

The living-body cover member 101 has further an adhesive part 105 at its opening for heightening closing ability therein other than the tightening part 102. The adhesive part 105 is made of a material adhering the living-body's skin and mucous membrane, and is suitably provided on the face contacting the skin and mucous membrane by a single or plural combination. The adhesive part 105 is preferably a viscoelastic gel of polyurethane or silicone rubber, and such a part is optimum which is exchangeable each time when viscosity becomes weak.

The gas mist supply port 103 communicates with the inside of the living-body cover member 101 for leading the gas mist and gas into the inside of the cover member 101. The gas mist supply port 103 is connected with a supply means of the gas mist and gas of the gas mist supply means 31 and the gas supply means 11 for leading the gas mist and gas into the inside of the living-body cover member 101. The check valve is provided inside of the gas mist supply port 103 for checking flow-back of the gas mist and gas.

The outlet 104 is an air hole of exhausting air, the gas mist and gas when taking out air from the living-body cover member 101 or when adjusting pressure by drawing out gas or the mist therein. The outlet 104 has such a structure stopping usually air flow by a valve or cap, and allowing it by getting out the valve or cap only when taking out air. The pressure control may be carried out manually, but as later mentioned, desirably automatically by a control device 51 together with supply control of gas and the gas mist based on measuring values of a manometer 61. A safety valve (recess valve) may be provided as the outlet 104 for automatically opening a valve when the inside of the living-body pressure bath cover 41 becomes more than a constant pressure.

The living-body cover member 101 is inside installed with a manometer 61 for measuring an inside pressure. The control device 51 controls supply of the gas mist and gas on the basis of measuring values of the manometer 61 for maintaining a pressure value within the gas mist pressure bath cover 100 to be more than 1 air pressure (more preferably, around 1.02 to 2.5 air pressure). For example, the control device 51 controls or stops the supply of gas or the gas mist from the gas supply means 11 and the gas mist supply device 31, or exhausts the gas mist or gas from the cover 100. Further, the gas mist pressure bath cover 100 is inside installed with a thermometer 62 for measuring an inside temperature within the cover 100. The control device 51 performs on-off of a heater installed in the liquid supply means 21 on the basis of measuring values of a manometer 62 for maintaining a predetermined temperature (for example, around 38° C.) bringing about warm bath effects within the gas mist pressure bath cover 100.

Now, explanation will be made to the above mentioned gas mist pressure bath system and a method of performing the gas mist pressure bath using the gas mist pressure bath cover 100 of this invention. At first, the bag shaped living-body cover member 101 is expanded, and a living-body's part requesting the gas mist pressure bath (herein, the living-body's hand) is inserted into the cover member 101. Next, the string 102*a* of the tightening part 102 is pulled to tighten and fix the string 102*a* by the string stopper 102*b*. Further on, the cover member 101 is adhered around a wrist with the adhesive part 105 of the opening so that the inside of the cover member 101 is made almost sealed. Air is in advance exhausted as much as possible from the outlet 104. Gas is supplied from the gas supply means 11 to the gas mist supply means 31, while liquid is supplied from the liquid supply means 21 to the same. At this time, the control device 51 controls the liquid and gas supplying pressure, amount and temperature. Thereby, the gas mist supply means 31 generates the gas mist, and the generated gas mist is supplied from the supply port 103 to the inside of the living-body cover member 101. When the mist is enough supplied in the cover member 101, only gas is supplied into the cover 101 from the gas mist supply means 11.

The control device 51 is controlled such that the inside of the living-body pressure bath cover 41 becomes an optimum pressurized and heated conditions (around 1.02 to 2.5 air pressure and around 38° C.) in view of the measuring values of the manometer 61 and the thermometer 62, and when pressure becomes too high, or when the gas mist and air are exchanged, it is possible to easily exhaust air from the outlet 104. Under such conditions, the optimum gas mist pressure bath is carried out.

Figure 4:
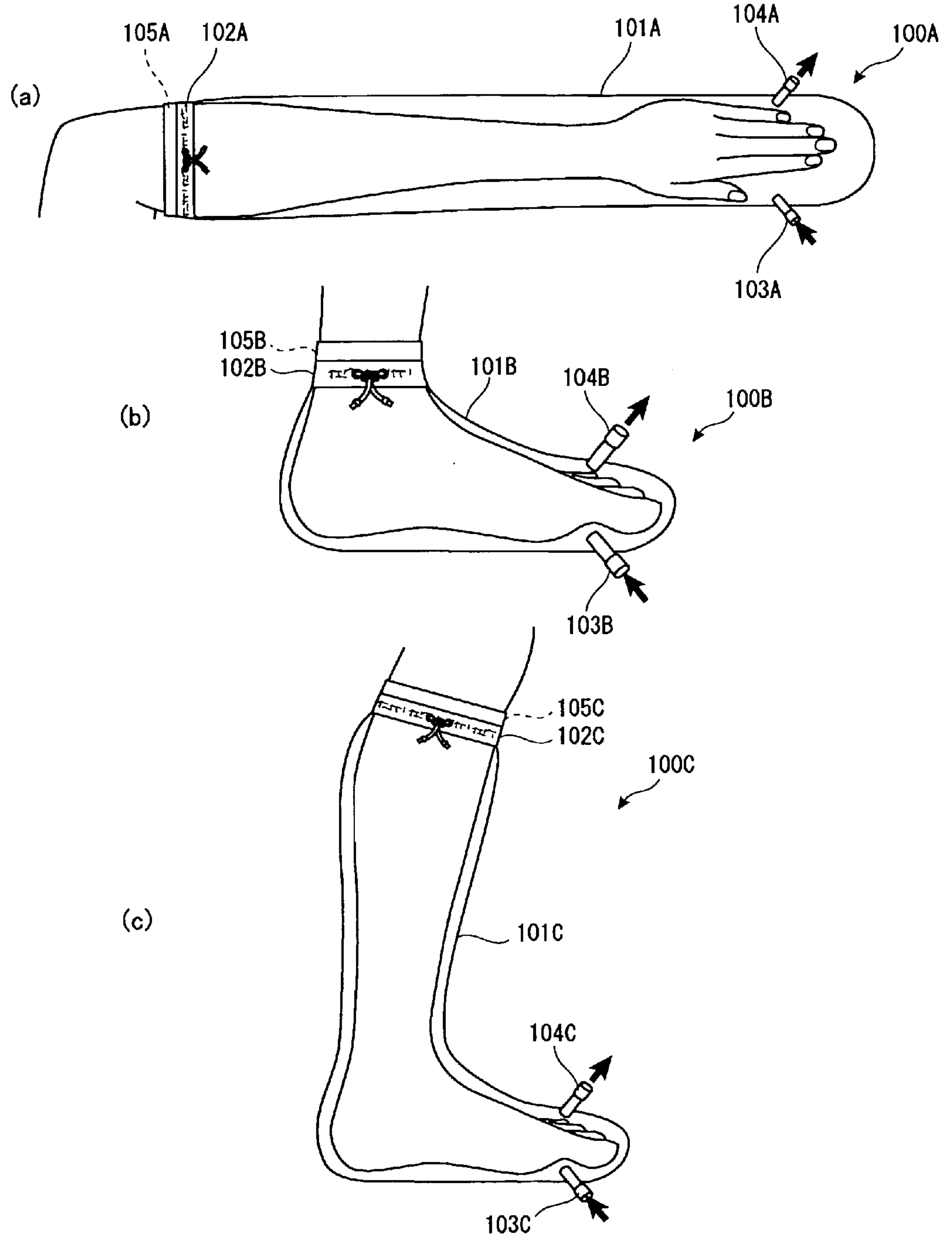
FIG. 4 Typical views showing other attaching conditions of the cover for the gas mist pressure bath depending on the first embodiment of the invention.

In the above embodiment, explanation has been made, taking up the examples of the living body's hand (the fingers, back and palm) as the parts to be performed with the gas mist pressure bath, but the gas mist pressure bath cover of the invention can be applied to other various parts of the living body. FIG. 4 is the typical views showing other attaching conditions of the cover for the gas mist pressure bath depending on the first embodiment of the invention.

While FIG. 3 is the gas mist pressure bath cover of the short glove shape for covering the fingers, back and palm of the hand, FIG. 4(*a*) shows a gas mist pressure bath cover 100A of a gauntlet shape for covering also a forearm in addition to the hand. This gauntlet shaped gas mist pressure bath cover 100A is also composed of a living-body cover member 101A, a tightening part 102A, a gas mist supply port 103A, an outlet 104A and an adhesive part 105A.

FIG. 4(*b*) shows a gas mist pressure bath cover 100B of a sock shape for a foot (toes, sole and instep). This sock shaped gas mist pressure bath cover 100B is also composed of a living-body cover member 101B, a tightening part 102B, a gas mist supply port 103B, an outlet 104B and an adhesive part 105B.

While FIG. 4(*b*) is the gas mist pressure bath cover 100B of the sock shape for covering the foot toes, sole and instep, FIG. 4(*c*) shows a gas mist pressure bath cover 100C of a stocking shape for covering also a heel and a lower limb in addition to the foot. This stocking shaped gas mist pressure bath cover 100C is also composed of a living-body cover member 101C, a tightening part 102C, a gas mist supply port 103C, an outlet 104C and an adhesive part 105C.

Second Embodiment

Figure 5:
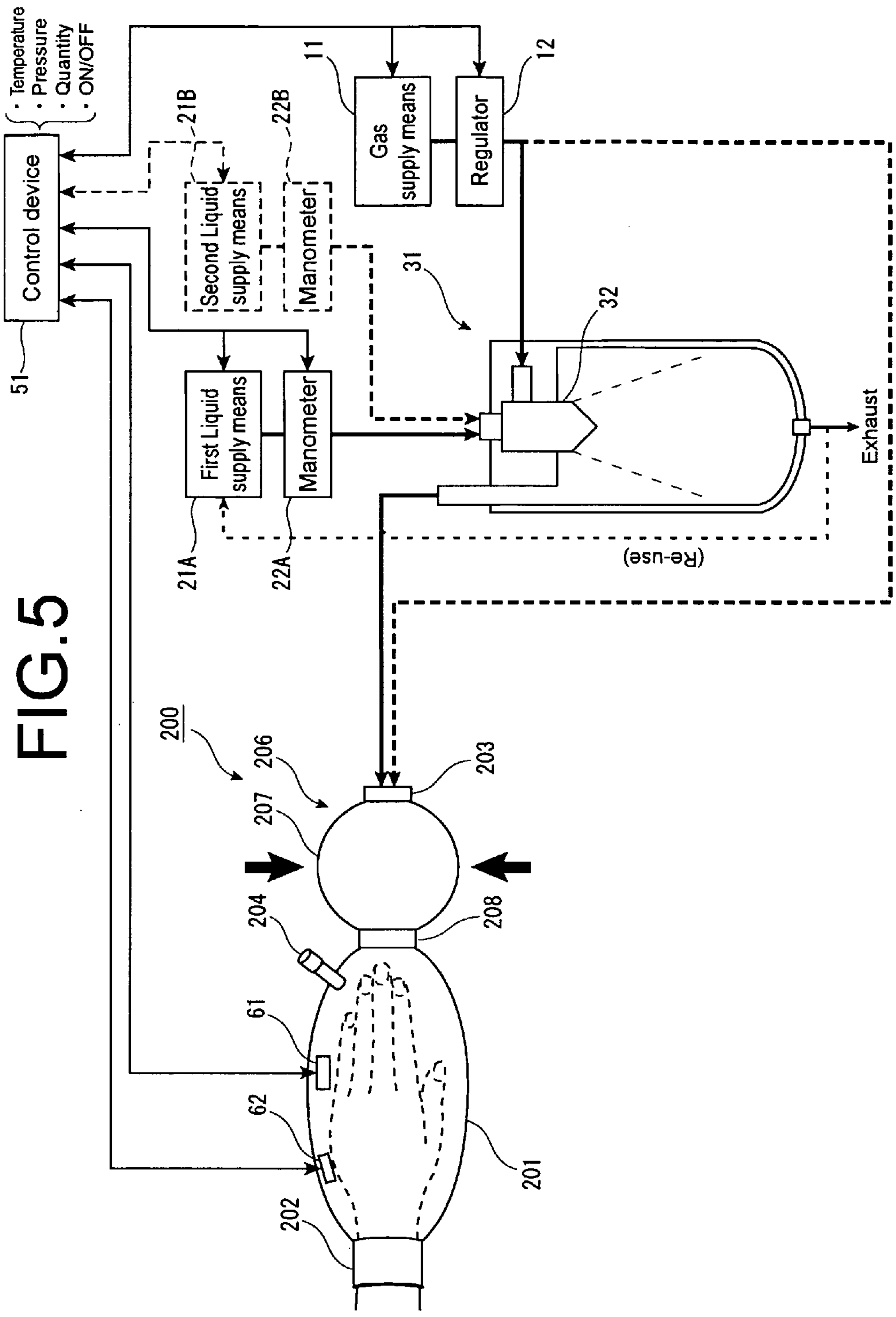
FIG. 5 A typical view showing one example of the gas mist pressure bath system applied with the cover for the gas mist pressure bath depending on a second embodiment of the invention.

FIG. 5 is the typical view showing one example of the gas mist pressure bath system applied with the cover for the gas mist pressure bath depending on the second embodiment of this invention. This embodiment will explain the cover for the gas mist pressure bath further having a pressurizing means for easily pressurizing the inside of the living-body cover. As to the same parts as those of the first embodiment shown in FIG. 1, the same numerals will be given, and detailed explanation will be omitted.

As shown in FIG. 5, the cover 200 for the gas mist pressure bath of this embodiment has the pressurizing part 206 for pressurizing the inside of the living-body cover member 201, other than the living-body cover member 201 of covering the skin and mucous membrane of the living body and forming the space for sealing inside the gas mist and gas.

Figure 6:
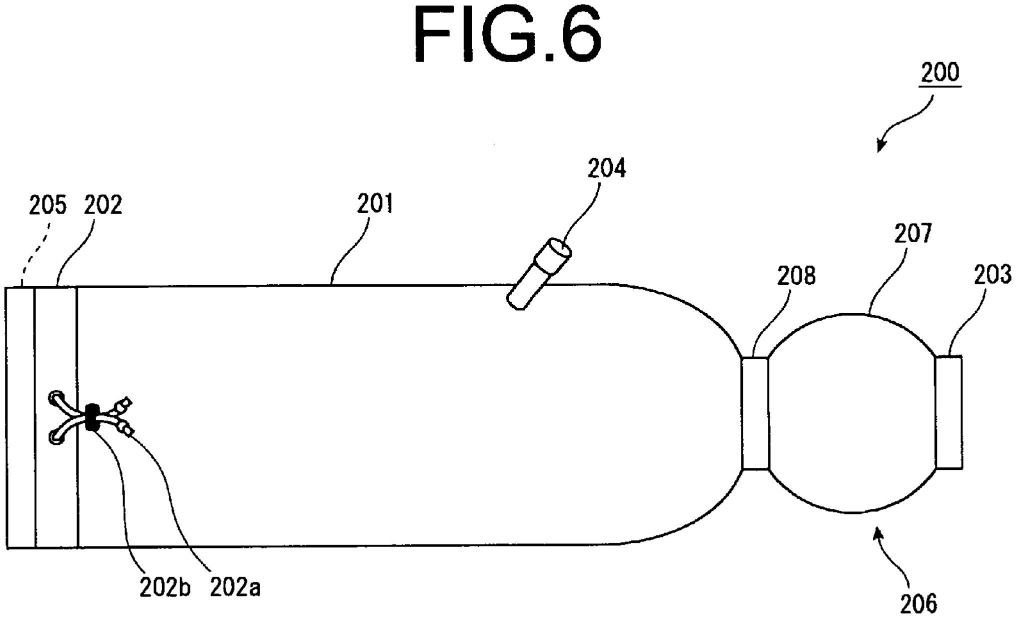
FIG. 6 A generally schematic view of the cover for the gas mist pressure bath depending on the second embodiment of the invention.
Figure 7:
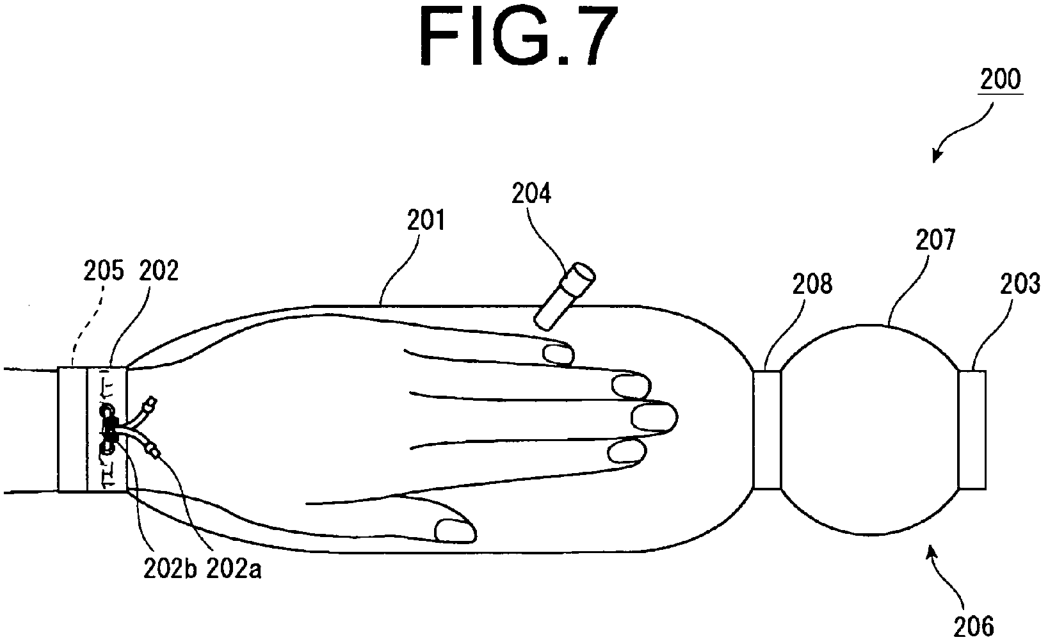
FIG. 7 A typical view showing an attaching condition of the cover for the gas mist pressure bath depending on the second embodiment of the invention.

In the following, explanation will be more concretely made to the gas mist pressure bath cover 200 based on FIGS. 6 and 7. FIG. 6 is the generally schematic view of the gas mist pressure bath cover depending on the present embodiment. FIG. 7 is the typical view showing an attaching condition of the gas mist pressure bath cover.

As showing in these figures, the gas mist pressure bath cover 200 is composed of the bag shaped living-body cover member 201 for covering the skin and mucous membrane of the living body (herein, as the example, the hand); the tightening part 202 provided at the opening of the living-body cover member 201 and closing the opening to prevent the gas mist and gas from running away; the gas mist supply port 203 having inside the check valve and introducing the gas mist and gas into the inside of the gas mist pressure bath cover 200 via the pressurizing part 206; the outlet 204 for controlling or discharging the amounts of air or the gas mist and gas in the gas mist pressure bath cover 200; the adhesive part 205 for heightening the closing ability within the living-body cover member 201; and the pressurizing part 206 for pressurizing the inside of the living-body cover member 201. The pressurizing part 206 is composed of the hollow air storage 207 communicating with the living-body cover member 201 and a connection part 208 connecting the air storage 207 and the living-body cover member 201.

The living-body pressure bath cover 201 is composed of the bag member having a size enabling to cover the living body (herein, as the example, the living body's hand). The living-body cover member 201 is made of the woven or non-woven fabric of a non-expansible, non-air permeable and non-moisture permeable material, for example, preferably, the natural rubber, silicone rubber, polyethylene, polypropylene, polyvinylidene, polystylene, polyvinylacetate, polyvinyl chloride, polyamide resin, polytetrafluoroethylene.

The living-body cover member 201 is furnished at its opening with the tightening part 202 to prevent the gas mist and gas from exhausting. Herein, as the example, the tightening means 202 is composed of the string 202*a* and the string stopper 102*b*. Other than the string 202*a*, the rubber or the face fastener may compose the tightening means by a single or plural combination.

The living-body cover member 201 has further an adhesive part 205 at its opening for heightening the closing ability therein other than the tightening part 202. The adhesive part 205 is made of a material adhering the living-body's skin and mucous membrane, and is suitably provided on the face contacting the skin and mucous membrane by a single or plurality of combination. The adhesive part 205 is preferably a viscoelastic gel of polyurethane or silicone rubber, and such a part is optimum which is exchangeable each time when viscosity becomes weak.

The gas mist supply port 203 communicates with the inside of the living-body cover member 200 for leading the gas mist and gas into the inside of the living-body cover member 201. The gas mist supply port 203 is connected with a supply means of the gas mist and gas of the gas mist supply means 31 and the gas supply means 11 for leading the gas mist and gas into the inside of the living-body cover member 201. The check valve is provided inside of the gas mist supply port 203 for checking flow-back of the gas mist and gas. By the way, in the gas mist pressure bath cover 200 shown in FIGS. 5 to 7, the gas mist and gas from the gas mist supply means 31 and the gas supply means 11 are at first supplied from the supply port 203 to the pressurizing part 206, and supplied into the living-body cover member 201 via the connection part 208.

The outlet 204 is an air hole of exhausting air, the gas mist and gas when taking out air from the gas mist pressure bath cover 200 or when adjusting pressure by drawing out gas or the gas mist therein. The outlet 204 has such a structure stopping usually air flow by a valve or cap, and allowing it by getting out the valve or cap only when taking out air. The pressure control may be carried out manually, but desirably automatically by a control device 51 together with supply control of gas and the gas mist based on measuring values of a manometer 61. A safety valve (recess valve) may be provided as the outlet 204 for automatically opening a valve when the inside of the living-body pressure bath cover 201 becomes more than a constant pressure.

The pressurizing part 206 is a means for pressurizing the inside of the living-body cover member 201, and herein is composed of a hollow air storage 207 communicating with the living-body cover member 201 and the connection part 208 connecting the air storage 207 and the living-body cover member 201. The pressurizing part 206 introduces the gas mist and gas into the living-body cover member 201, and at the same time stores the gas mist and gas also in the air storage 207, and if pressurizing as crushing the air storage 207 as showing with arrows in FIG. 5, the gas mist or gas in the air storage 207 is exhausted into the living-body cover member 201 via the connection part 208. Thereby, the inside of the living body cover member 201 can be pressurized. The inside of the connection part 208 is provided with the check valve for checking back-flow of the gas mist and gas.

The air storage 207 may be structured as pressurizing manually, and mechanically by controlling the control means 51 using a driving device. Pressurization in the gas mist pressure bath heightens effects by performing an interval pressurization in pulse, and so the air storage 207 may be pressed intermittently at constant rhythm. The pressurizing interval heightens effects by synchronizing with pulsation of pulse.

The living-body cover member 201 is inside installed with a manometer 61 for measuring an inside pressure. The control device 51 controls supply of the gas mist and gas on the basis of measuring values of the manometer 61 for maintaining a pressure value within the gas mist pressure bath cover 200 to be more than 1 air pressure (more preferably, around 1.02 to 2.5 air pressure). For example, the control device 51 controls or stops the supply of gas or the gas mist from the gas supply means 11 and the gas mist supply device 31, or exhausts the gas mist or gas from the gas mist pressure bath cover 200. Further, the gas mist pressure bath cover 200 is inside installed with the thermometer 62 for measuring an inside temperature within the gas mist pressure bath cover 200. The control device 51 performs on-off of a heater installed in the liquid supply means 21 on the basis of measuring values of the manometer 62 for maintaining a predetermined temperature (for example, around 38° C.) bringing about warm bath effects within the gas mist pressure bath cover 200.

Explanation will be made to the above mentioned gas mist pressure bath system and a method of performing the gas mist pressure bath using the gas mist pressure bath cover 200 of this invention. At first, the bag shaped living-body cover member 201 is expanded, and a part of the living-body requesting the gas mist pressure bath (herein, the hand) is inserted into the cover member 201. Next, the string 202*a* of the tightening part 202 is pulled to tighten and fix the string 202*a* by the string stopper 202*b*. Further on, the cover member 201 is adhered around a wrist with the adhesive part 205 of the opening so that the inside of the cover member 201 is made almost sealed. Air is in advance exhausted as much as possible from the outlet 204. Gas is supplied from the gas supply means 11 to the gas mist supply means 31, while liquid is supplied from the liquid supply means 21 to the same. At this time, the control device 51 controls the liquid and gas supplying pressure, amount and temperature. Thereby, the gas mist supply means 31 generates the gas mist, and the generated gas mist is supplied from the supply port 203 to the inside of the living-body cover member 201 via the air storage 207 and the connection part 208. When the mist is enough supplied in the cover member 201, only gas is supplied into the cover 201 from the gas mist supply means 11. The control device 51 is controlled such that the inside of the living-body pressure bath cover member 201 becomes an optimum temperature (around 38° C.). When the gas mist or gas of the optimum amount is stored in the living-body cover member 201 and the air storage 207, the control device 51 once stops the supply of the gas mist or gas. The air storage 207 is pressurized as crushed. Thereby, the gas mist or gas in the air storage 207 is exhausted into the living-body cover member 201, and the inside of the living-body cover member 201 is moderately pressurized (around 1.02 to 2.5 air pressure), and the gas mist pressure bath is carried out. When pressure becomes too high, or when the gas mist and gas are exchanged, it is possible to easily exhaust air from the outlet 204. Under such conditions, the optimum and heated conditions.

Figure 8:
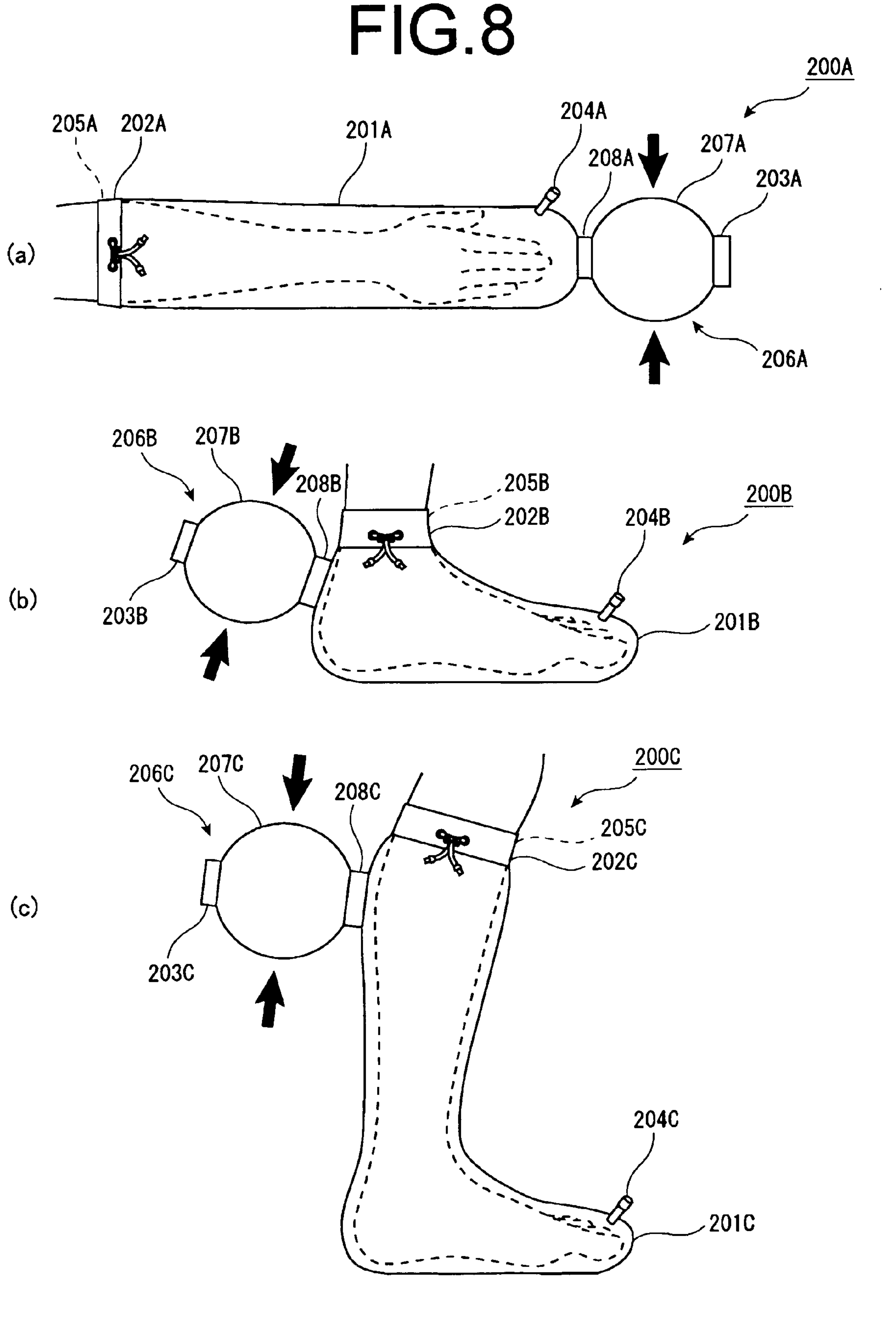
FIG. 8 Typical views showing other attaching conditions of the cover for the gas mist pressure bath depending on the second embodiment of the invention.

In the above embodiment, explanation has been made, taking up the examples of the living body's hand (the fingers, back and palm) as the parts to be performed with the gas mist pressure bath, but the gas mist pressure bath cover of the invention can be applied to other various parts of the living body. FIG. 8 are the typical views showing other attaching conditions of the cover for the gas mist pressure bath depending on the first embodiment of the invention.

While FIG. 5 is the gas mist pressure bath cover of the short glove shape for covering the fingers, back and palm of the hand, FIG. 8(*a*) shows a gas mist pressure bath cover 200A of a gauntlet shape for covering also a forearm in addition to the hand. This gauntlet shaped gas mist pressure bath cover 200A is also composed of a living-body cover member 201A, a tightening part 202A, a gas mist supply port 203A, an outlet 204A, an adhesive part 205A, and a pressurizing part 206A (air storage 207A and connection part 208A).

FIG. 8(*b*) shows a gas mist pressure bath cover 200B of a sock shape for a foot (toes, sole and instep). This sock shaped gas mist pressure bath cover 200B is also composed of a living-body cover member 201B, a tightening part 102B, a gas mist supply port 203B, an outlet 204B and an adhesive part 205B.

While FIG. 8(*b*) is the gas mist pressure bath cover 200B of the sock shape for covering the foot toes, sole and instep, FIG. 8(*c*) shows a gas mist pressure bath cover 200C of a stocking shape for covering also a heel and a lower limb in addition to the foot. This stocking shaped gas mist pressure bath cover 200C is also composed of a living-body cover member 201C, a tightening part 202C, a gas mist supply port 203C, an outlet 204C, an adhesive part 205C, and a pressurizing part 206A (air storage 207A and the connection part 208A).

In the above embodiment, the pressurizing part is composed of the hollow air storage communicating with the living-body cover member via the connection part, but as far as enabling to easily pressurize the inside of the living-body cover member, any members are sufficient. In the following, other composing examples of the pressurizing part will be explained.

Figure 9:
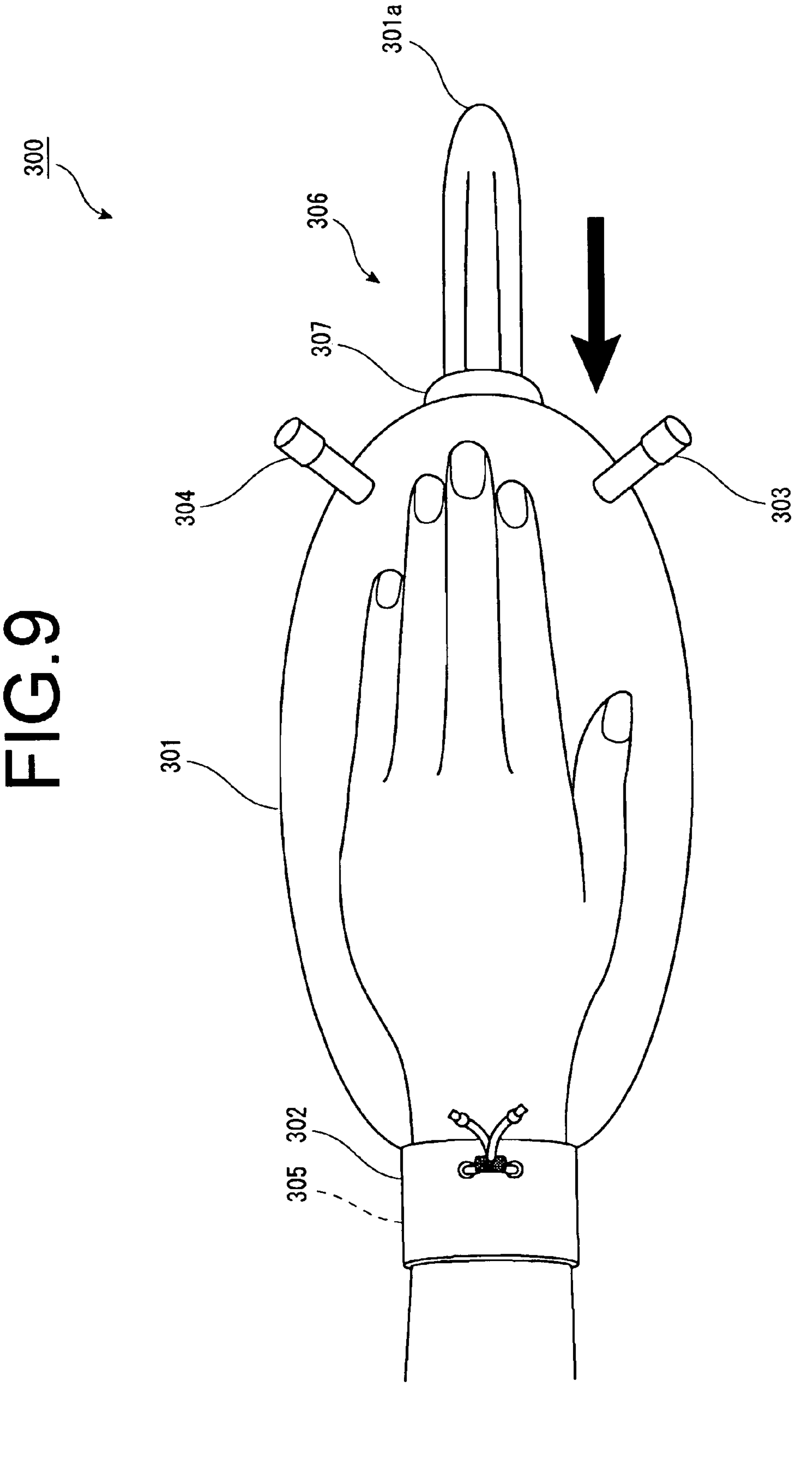
FIG. 9 A typical view (No. 1) showing the other attaching condition of the cover for the gas mist pressure bath depending on the second embodiment of the invention.

FIG. 9 is the typical view (No. 1) showing an example of another pressurizing part for pressurizing the cover for the gas mist pressure bath depending on the second embodiment of the invention. Herein, reference will be made to the living-body cover member cover 300 where the pressurizing part 306 is composed of the reducing ring 307 reducing the living-body cover member. In the following, other than that the living-body cover member 301, the supply port 303 and the pressurizing part 306 are different in the compositions, since there are the same compositions as those of FIG. 5, detailed explanations for respective parts other than the above mentioned will be omitted.

The gas mist pressure bath cover 300 is composed of the bag shaped living-body cover member 301; the tightening part 302 provided at the opening of the living-body cover member 301 and closing the opening to prevent the gas mist and gas from running away; the gas mist supply port 303 having inside a check valve, communicating with the living-body cover member 301 and introducing the gas mist and gas into the inside of the gas mist pressure bath cover 300; the outlet 304 for controlling or discharging the amounts of air or the gas mist and gas in the gas mist pressure bath cover 300; the adhesive part 305 for heightening closing ability within the living-body cover member 301; and the pressurizing part 306 for pressurizing the inside of the living-body cover member 301.

The pressurizing part 306 is composed of the reducing ring 307 formed with an elastic member as a rubber and having a small hole. The reducing ring 307 is passed into its small hole with a front end portion (bag bottom) 301*a* of the bag shaped living-body cover member 301, and if sliding in an arrow direction of FIG. 9, the vicinity of the front end portion (bag bottom) 301*a* is reduced by the small hole of the reducing ring 307, so that the space of storing the gas mist and gas of the living-body cover member 301 is made narrow and the inside of the living-body cover member 301 is pressurized.

Herein, as the pressurizing part 306, a clip may be used instead of the reducing ring 307. In short, any means may be sufficient, as far as being possible to reduce the living-body cover member 301 at the front end portion 301*a* so that the space of storing the gas mist and gas of the living-body cover member 301 is made narrow and the inside of the living-body cover member 301 is pressurized.

The pressurizing part 306 (reducing ring 307) may be structured manually slid and fixed, or mechanically by controlling the control device 51. Pressurization by sliding the pressurizing part 306 (reducing ring 307) may be performed by specific interval in pulse. Further on, illustration has been made, taking up the examples of the living body's hand parts, but it is of course to apply to other various parts of the living body.

Figure 10:
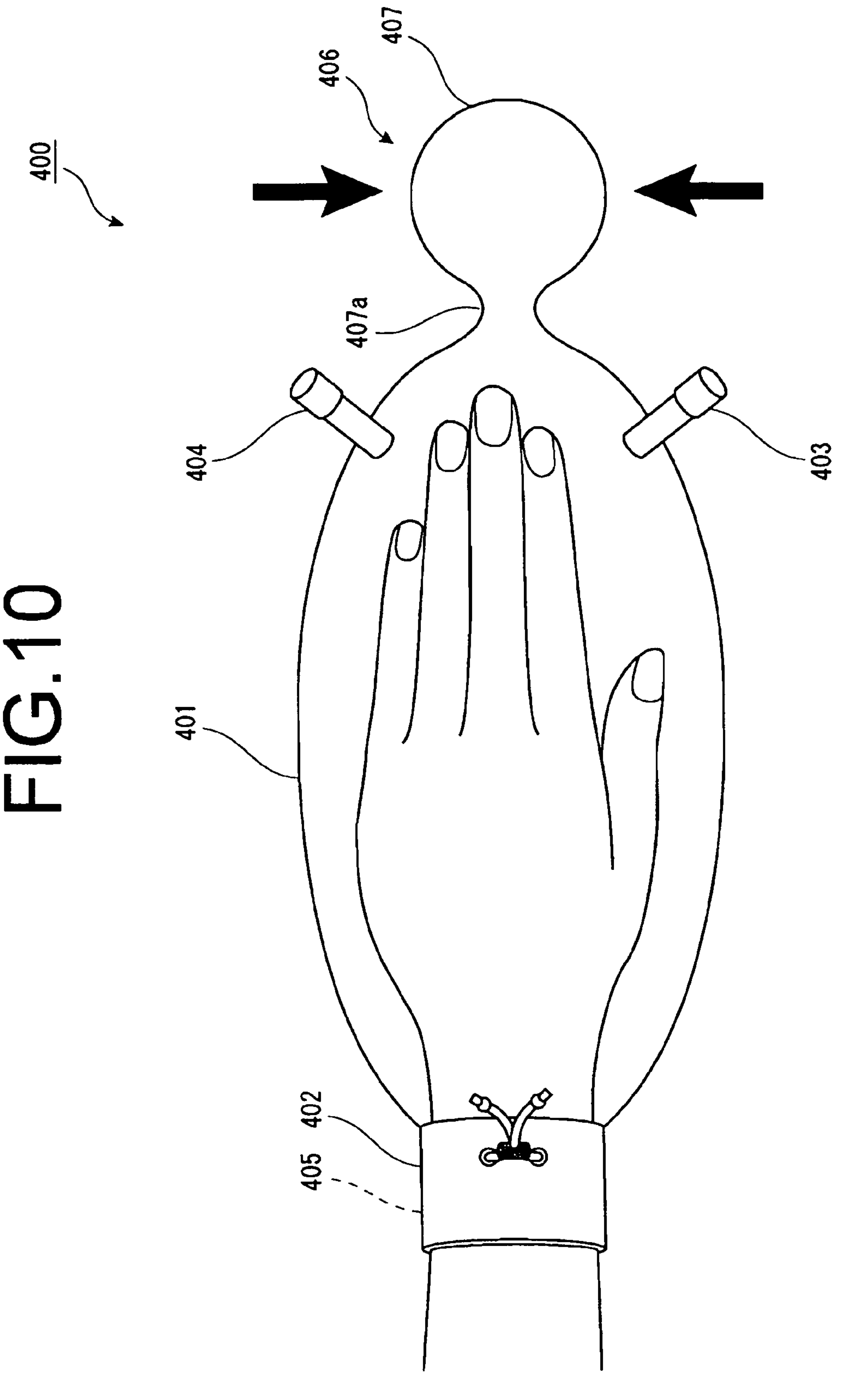
FIG. 10 A typical view (No. 2) showing an attaching condition of the cover for the gas mist pressure bath depending on the second embodiment of the invention.

Next reference will be made to the cover 400 for the gas mist pressure bath where the pressurizing part 406 is composed of an almost spherical hollow air storage 407. FIG. 10 is the typical view (No. 2) showing another pressurizing part of the cover for the gas mist pressure bath depending on the second embodiment of the invention. In the following, other than that the living-body cover member 301, the supply port 403 and the pressurizing part 406 are different in the compositions, since there are the same compositions as those of FIG. 5, detailed explanations for respective parts other than the above mentioned will be omitted.

The gas mist pressure bath cover 400 is composed of the bag shaped living-body cover member 401; the tightening part 402 provided at the opening of the living-body cover member 401 and closing the opening to prevent the gas mist and gas from running away; the gas mist supply port 403 having inside a check valve, communicating with the living-body cover member 401 and introducing the gas mist and gas into the inside of the gas mist pressure bath cover 400; the outlet 404 for controlling or discharging the amounts of air or the gas mist and gas in the gas mist pressure bath cover 400; the adhesive part 405 for heightening closing ability within the living-body cover member 401; and the pressurizing part 406 for pressurizing the inside of the living-body cover member 401.

The pressurizing part 406 is composed of the almost spherical hollow air storage 407 communicating with the living-body cover member 401. As shown in FIG. 10, a narrow part 407*a* sections in shape the pressurizing part 406 from the living-body cover member 401. By pressurizing as crushing the air storage 407, the gas mist or gas is exhausted into the living-body cover member 401, and the inside of the living body cover member 401 can be moderately pressurized.

The air storage 407 may be furnished with an exclusively used cover for covering the whole of the air storage 407. The air storage 407 may be structured as pressurizing manually, or mechanically by the control means 51. Pressurization by the pressurizing part 406 may be performed by specific interval in pulse. Further on, illustration has been made, taking up the examples of the living body's hand parts, but it is of course to apply to other various parts of the living body.

Figure 11:
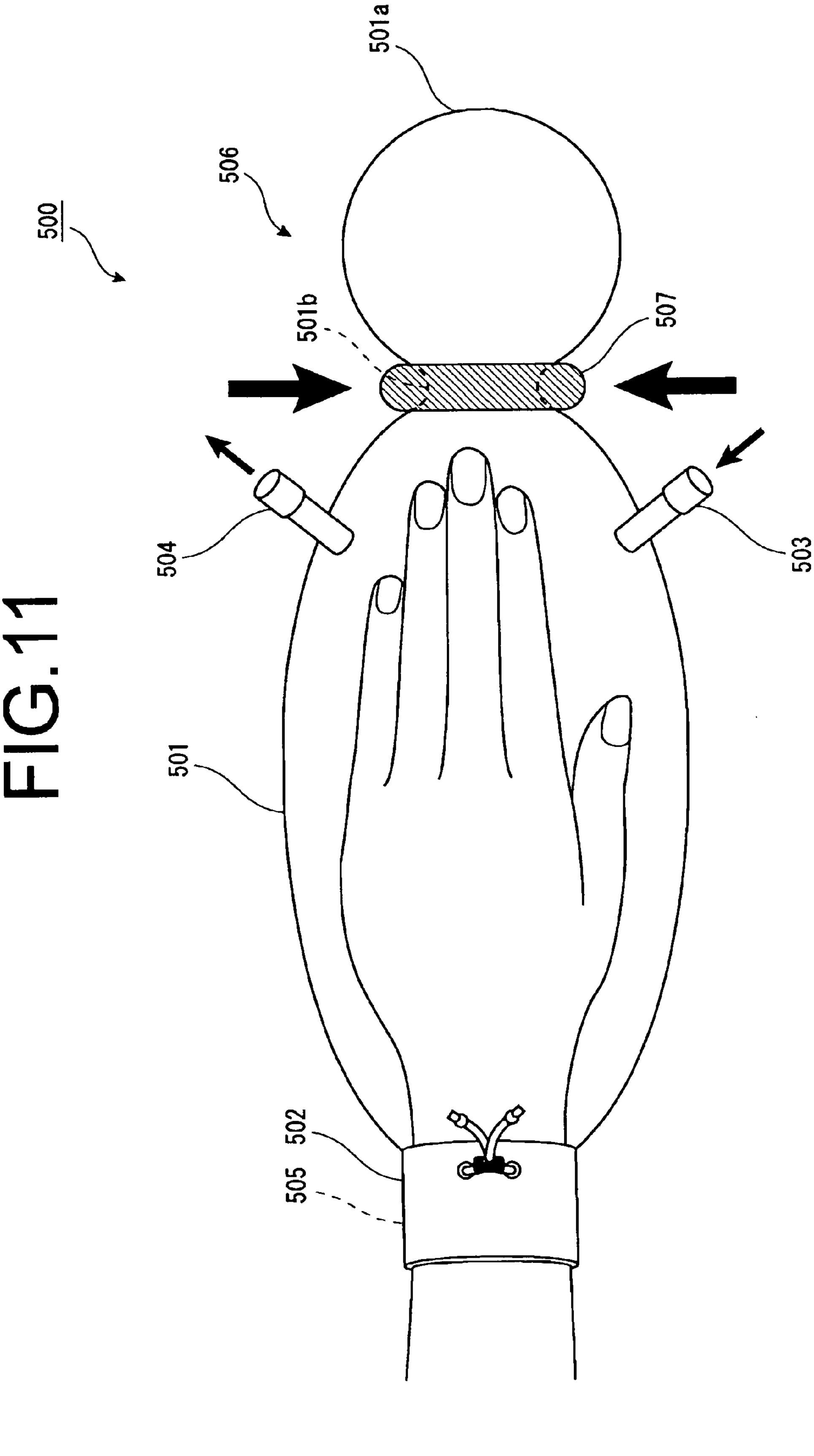
FIG. 11 A typical view (No. 3) showing a further attaching condition of the cover for the gas mist pressure bath depending on the second embodiment of the invention.

Next reference will be made to the cover 500 for the gas mist pressure bath where the pressurizing part 506 is composed of a pressurizing ring 507 of pressurizing the living-body cover member 501 outside. FIG. 11 is the typical view (No. 3) showing another pressurizing part of the cover for the gas mist pressure bath depending on the second embodiment of the invention. In the following, other than that the living-body cover member 501, the supply port 503 and the pressurizing part 506 are different in the compositions, since there are the same compositions as those of FIG. 5, detailed explanations for respective parts other than the above mentioned will be omitted.

The gas mist pressure bath cover 500 is composed of the bag shaped living-body cover member 501; the tightening part 502 provided at the opening of the living-body cover member 501 and closing the opening to prevent the gas mist and gas from running away; the gas mist supply port 503 having inside a check valve, communicating with the living-body cover member 501 and introducing the gas mist and gas into the inside of the gas mist pressure bath cover 500; the outlet 504 for controlling or discharging the amounts of air or the gas mist and gas in the gas mist pressure bath cover 500; the adhesive part 505 for heightening closing ability within the living-body cover member 501; and the pressurizing part 506 for pressurizing the inside of the living-body cover member 501.

The pressurizing part 506 is composed of the pressurizing ring 507 having a hole at its center, and made of an elastic member as a rubber or a coil spring. The pressurizing ring 507 is passed into its central hole with a front end portion (bag bottom) 501*a* of the bag shaped living-body cover member 501, and the living-body cover member 501 is pressurized outside by shrinking force of the pressurizing ring 507. Preferably, the living-body cover member 501 is in advance formed with the narrow part 501*b* for checking sliding of the pressurizing ring 507 (outer diameter of the narrow part 501*b*> hole diameter of the pressurizing ring 507). This narrow part 501*b* is applied with the pressurizing ring 507 and if its shrinking force pressurizes outside the narrow part 501*b*, the inside of the living body cover member 401 can be moderately pressurized.

Herein, as the pressurizing part 506, the clip may be used instead of the reducing ring 507. In short, any means may be sufficient, as far as being possible to pressurize the living-body cover member 501 outside for pressurizing the inside of the living-body cover member 501.

Further on, illustration has been made, taking up the examples of the living body's hand parts, but it is of course to apply to other various parts of the living body.

Figure 12:
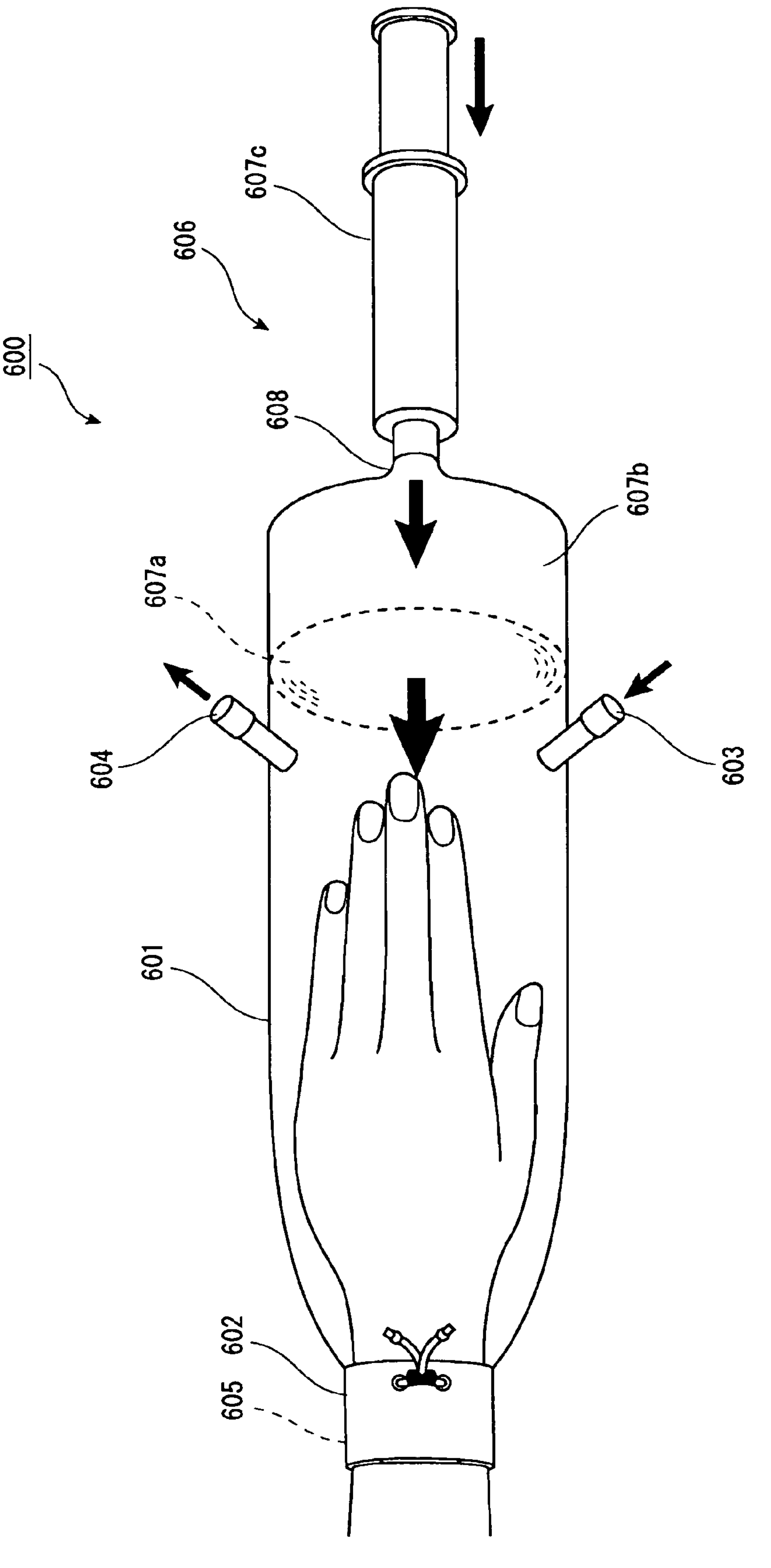
FIG. 12 A typical view (No. 4) showing a still further attaching condition of the cover for the gas mist pressure bath depending on the second embodiment of the invention.

Next, explanation will be made to the cover 600 for the gas mist pressure bath composed of the air storage 607*b* where the pressurizing part 606 is mainly provided within the living-body cover member 601, and a pump (syringe) 607*c*. FIG. 12 is the typical view (No. 4) showing another pressurizing part of the cover for the gas mist pressure bath depending on the second embodiment of the invention. In the following, other than that the living-body cover member 601, the supply port 603 and the pressurizing part 606 are different in the compositions, since there are the same compositions as those of FIG. 5, detailed explanations for respective parts other than the above mentioned will be omitted.

The gas mist pressure bath cover 600 is composed of the bag shaped living-body cover member 601; the tightening part 602 provided at the opening of the living-body cover member 601 and closing the opening to prevent the gas mist and gas from running away; the gas mist supply port 603 having inside a check valve, communicating with the living-body cover member 601 and introducing the gas mist and gas into the inside of the gas mist pressure bath cover 600; the outlet 604 for controlling or discharging the amounts of air or the gas mist and gas in the gas mist pressure bath cover 600; the adhesive part 605 for heightening closing ability within the living-body cover member 601; and the pressurizing part 606 for pressurizing the inside of the living-body cover member 601.

The pressurizing part 606 is composed of the shielding film 607*a* sectioning the inside of the living-body cover member 601 into the air storage 607*b*, the air storage 607*b* in the living-body cover member 601 sectioned by the shielding film 607*a*, and the syringe 607*c* for inletting air into the air storage 607*b*. Numeral 608 designates an air inlet connecting the air storage 607*b* and the syringe 607*c*.

The shielding film 607*a* is composed of a material having elasticity, pressure resistance, or non-moisture permeability (for example, silicone rubber or latex rubber), sectioning the inside of the living-body cover member 601 into the air storage 607*b*. The air storage 607*b* is formed with the air inlet 608 for connecting the syringe 607*c*. Preferably, the air inlet 608 is arranged with the check valve for checking air back-flow. By sending air by the syringe 607*c* into the air storage 607*b* sectioned by the shielding film 607*a*, the shielding film 607*a* made of the elastic material is expanded toward the insertion side of the living-body. Thereby, since the space of storing the gas mist and gas of the living-body cover member 601, the inside of the living-body cover member 601 is pressurized.

The syringe 607*c* of the pressurizing part 606 may be structured as pressurizing manually, or mechanically by the control means 51. Actuation of the syringe 607*c* may be performed by specific interval in pulse. Further on, illustration has been made, taking up the examples of the living body's hand parts, but it is of course to apply to other various parts of the living body.

Each of the above mentioned embodiments has shown the example of applying the cover for the gas mist pressure bath to the human living-body, but the invention may be applied not only to the human living body but to animals.

With the structure as mentioned above, according to the present invention, it is possible to cause the gas mist to be efficiently absorbed into the skin and mucous membrane of the living body, while easily carrying about exhaust of air in the gas mist pressure bath cover and control of pressure in the cover.

The above explanation has been made to the embodiments of the invention, but the invention is not limited to such embodiments, and so far as not deviating from the subject matter of the invention, various kinds of embodiments are, of course, available.

INDUSTRIAL APPLICABILITY

Thus, the present invention relates to the cover for the gas mist pressure bath, in which the gas mist is prepared by pulverizing and dissolving carbon dioxide or oxygen and liquid, or a mixed gas of carbon dioxide and oxygen and liquid, and is caused to contact the skin and mucous membrane of the living-body at pressure of not less than a predetermined value, having industrial applicability.

DESCRIPTION OF SYMBOLS

11: Gas supply means,
12: Regulator,
21, 21A, 21B: Liquid supply means,
22, 22A, 22B: Manometer,
31: Gas mist supply means,
32: Fluid nozzle,
51: Control device,
61: Manometer,
62: Thermometer,
100, 100A, 100B, 100C, 200, 200A, 200B, 200C, 300, 400, 500, 600: Cover for the gas mist pressure bath,
101, 101A, 101B, 101C, 201, 201A, 201B, 201C, 301, 401, 501, 601: Living-body cover member,
102, 102A, 102B, 102C, 202, 202A, 202B, 202C, 302, 402, 502, 602: Tightening part,
102*a*, 202*b*: String,
102*b*, 102*b*: String stopper,
103, 103A, 103B, 103C, 203, 203A, 203B, 203C, 303, 403, 503, 603: Gas mist supply port,
104, 104A, 104B, 104C, 204, 204A, 204B, 204C, 304, 404, 504, 604: Exhaust port
105, 105A, 105B, 105C, 205, 205A, 205B, 205C, 305, 405, 505, 605: Adhesive part,
206, 206A, 206B, 206C, 306, 406, 506, 606: Pressurizing part,
207, 207A, 207B, 207C, 407, 607*b*: Gas storage, Air storage,
208, 208A, 208B, 208C: Connection part,
301*a*, 501*a*: Front end (Bag bottom),
307: Reducing ring,
407*a*, 501*b*: Narrow part,
507: Pressurizing ring,
607*c*: Pump (Syringe),
607*a*: Shielding film, and
608: Air pouring port.

The invention claimed is:

1. A cover for a gas mist pressure bath adapted to prepare a gas mist by pulverizing and dissolving carbon dioxide or oxygen and liquid or a mixed gas of the carbon dioxide and oxygen and liquid at a density of not less than a predetermined value, and to directly contact the gas mist sealed in the cover to a skin and mucous membrane of a living-body, comprising:

a bag shaped living-body cover member for covering the skin and mucous membrane of the living body;

a tightening device disposed at one side of the living-body cover member to tighten an opening of the living-body cover member to prevent diffusion of the gas mist;

a gas mist supply port communicating with an inside of the cover for the gas mist pressure bath for introducing the gas mist into the cover;

an outlet attached to the living-body cover member for exhausting air, the gas mist or gas sealed in the cover for the gas mist pressure bath and controlling quantity of the air, gas mist, or gas; and a pressurizing device disposed on another side of the living-body cover member for pressurizing the inside of the living-body cover member, wherein the pressurizing device comprises a reducing ring formed with an elastic member, an end portion of the living-body cover member passes into a hole of the reducing ring and the reducing ring slides toward the tightening device, so that the reducing ring reduces an internal space of the living-body cover member at the end portion thereof to carry out the pressurization.

* * * * *